(12) United States Patent
Bradley et al.

(10) Patent No.: US 9,383,308 B2
(45) Date of Patent: *Jul. 5, 2016

(54) MULTI-COMPONENT REGRESSION/MULTI-COMPONENT ANALYSIS OF TIME SERIES FILES

(71) Applicant: Thermo Electron Scientific Instruments LLC, Madison, WI (US)

(72) Inventors: Michael S. Bradley, Edgerton, WI (US); Garry L. Ritter, Verona, WI (US); Alexander I. Grenov, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 565 days.

This patent is subject to a terminal disclaimer.

(21) Appl. No.: 13/654,146

(22) Filed: Oct. 17, 2012

(65) Prior Publication Data

US 2013/0096883 A1    Apr. 18, 2013

Related U.S. Application Data

(60) Provisional application No. 61/548,014, filed on Oct. 17, 2011.

(51) Int. Cl.
| | |
|---|---|
| *G06F 15/00* | (2006.01) |
| *G01N 21/35* | (2014.01) |
| *G01J 3/28* | (2006.01) |
| G01N 21/27 | (2006.01) |
| G01N 21/3504 | (2014.01) |
| G01N 21/3563 | (2014.01) |
| G01N 21/3577 | (2014.01) |

(52) U.S. Cl.
CPC .............. *G01N 21/35* (2013.01); *G01J 3/2803* (2013.01); *G01N 21/272* (2013.01); *G01N 21/3504* (2013.01); *G01N 21/3563* (2013.01); *G01N 21/3577* (2013.01); *G01N 2201/1293* (2013.01)

(58) Field of Classification Search
USPC ....................................................... 702/189
See application file for complete search history.

(56) References Cited

U.S. PATENT DOCUMENTS 7,072,770 B1 *  7/2006  Schweitzer .............. G01J 3/28
                                                    702/22
7,072,771 B2    7/2006  Oliveira
(Continued)

FOREIGN PATENT DOCUMENTS

| CN | 101981433 | 2/2011 | | |
|---|---|---|---|---|
| TW | I270005 | 1/2007 | | |
| WO | WO 2013/059310 | * | 4/2013 | ............. G01N 21/35 |

OTHER PUBLICATIONS

Brian K. Dable, Rapid multivariate curve resolution applied to near real-time process monitoring with HPLC/Raman data, Analytica Chimica Acta 544 (2005) , p. 71-81, Mar. 25, 2005, © 2005 Elsevier B.V.*

Boiana O. Budevska, Application of Multivariate Curve Resolution for Analysis of FT-IR Microspectroscopic Images of in Situ Plant Tissue, vol. 57, No. 2, 2003, p. 124-131.*

(Continued)

*Primary Examiner* — Tung S Lau
(74) *Attorney, Agent, or Firm* — Ion C. Abraham

(57) ABSTRACT

MCR provided estimated pure component time series spectra as extracted from infrared or other spectroscopy is capable of being compared to spectra in a reference library to find the best matches. The best match spectra can then each in turn be combined with the reference spectra, with the combinations also being screened for best matches versus any one of the estimated pure component time series spectra. These resulting best matches can then also undergo the foregoing combination and comparison steps. The process can repeat in this manner in an unbounded fashion if desired until an appropriate stopping point is reached, for example, when a desired number of best matches are identified, when some predetermined number of iterations has been performed, etc. This methodology is able to return best-match spectra with far fewer computational steps and greater speed than if all possible combinations of reference spectra are considered.

11 Claims, 5 Drawing Sheets

(56) References Cited

U.S. PATENT DOCUMENTS

| | | | |
|---|---|---|---|
| 7,698,098 B2* | 4/2010 | Ritter | G01N 21/35 250/282 |
| 2004/0148106 A1 | 7/2004 | Hahn et al. | |
| 2004/0220760 A1* | 11/2004 | Niu et al. | 702/76 |
| 2013/0096883 A1* | 4/2013 | Bradley | G01N 21/35 702/189 |

OTHER PUBLICATIONS

Budevska et al., "Application of Multivariate Curve Resolution for Analysis of FT-IR Microspectroscopic Images of in Situ Plant Tissue," Applied Spectroscopy vol. 57, No. 2 (2003), pp. 124-131.

Dable et al., "Rapid multivariate curve resolution applied to near real-time process monitoring with HPLC/Raman data," Analytica Chimica Acta 544 (2005), pp. 71-81.

* cited by examiner

| Spectrum Name: | | Film Sample | | | |
|---|---|---|---|---|---|
| Spectrum File: | | C:\MyDocuments\testresults\spectra\absorb.spa | | | |
| Spectrum Date: | | Fri Feb 15 2008 11:13:08 (CST) | | | |
| Rank / Index | Match Value | Source Index | Compound Name | Source of Compound | Cumulative Match | Weight |
|---|---|---|---|---|---|---|
| 1 | 99.58 | 2 | Polystyrene Film | User Library | 99.58 | 5.4195 |
| 2 | 68.97 | 10 | Toluene (Transmission Cell) | FTIRSearch.com | 56.96 | 5.7799 |
| | | 22 | ABS Plastic (ATR Corrected) | NIST Library | 68.92 | 29.3250 |
| | | 3 | Polytetrafluoroethylene Film | C:\MyDocuments\reference | 68.97 | 30.3022 |
| 3 | 68.93 | 10 | Toluene (Transmission Cell) | FTIRSearch.com | 56.96 | 5.7825 |
| | | 22 | ABS Plastic (ATR Corrected) | NIST Library | 68.92 | 29.4314 |
| | | 37 | Aspirin Tablet (DRIFTS) | Aldrich Library | 68.93 | 0.1370 |
| 4 | 68.87 | 10 | Toluene (Transmission Cell) | FTIRSearch.com | 56.96 | 5.8218 |
| | | 14 | ABS Plastic (ATR - Ge Crystal) | User Library | 68.82 | 84.5645 |
| | | 3 | Polytetrafluoroethylene Film | C:\MyDocuments\reference | 68.87 | 30.4534 |
| 5 | 68.83 | 10 | Toluene (Transmission Cell) | FTIRSearch.com | 56.96 | 5.8254 |
| | | 14 | ABS Plastic (ATR - Ge Crystal) | User Library | 68.82 | 64.8435 |
| | | 37 | Aspirin Tablet (DRIFTS) | Aldrich Library | 68.83 | 0.1211 |

FIG. 5

MULTI-COMPONENT REGRESSION/MULTI-COMPONENT ANALYSIS OF TIME SERIES FILES

BACKGROUND OF THE INVENTION

1. Field of the Invention

The present invention relates to the field of spectral analysis and, more specifically, toward the automatic identification of evolving time series spectra using Multi-component regression in combination with Multi-component spectral matching when desired.

2. Discussion of the Related Art

A molecular spectrometer (sometimes referred to as a spectroscope) is an instrument wherein a solid, liquid, or gaseous sample is illuminated, often with non-visible light such as light in the infrared region of the spectrum. The light from the sample is then captured and analyzed to reveal information about the characteristics of the sample. As an example, a sample may be illuminated with infrared light having a known intensity across a range of wavelengths, and the light transmitted and/or reflected by the sample can then be captured for comparison to the light source. Review of the captured spectra can then illustrate the wavelengths at which the illuminating light was absorbed by the sample. The spectrum, and in particular the locations and amplitudes of the peaks therein, can be compared to libraries of previously-obtained reference spectra to obtain information about the sample, such as its composition and characteristics. In essence, the spectrum serves as a "fingerprint" for the sample and for the substances therein, and by matching the fingerprint to one or more known fingerprints, the identity of the sample might be determined.

However, there are numerous occasions when time-dependent data is collected using such above described methods, such as, for example, in chemical reaction monitoring (kinetics), or thermal analysis with gas emission (TGA-IR) or chromatography (GC-IR). The most tedious step of this analysis is the extraction of independent spectra from the concatenated series of spectra followed by an analysis of these individual spectra. In GC-IR, the spectra are typically for pure components—the GC does the separation—but in TGA-IR, the individual spectra can also be mixtures themselves.

It is thus to be appreciated that if one wishes to compare a time series number of spectra of an evolving sample to all possible combinations of one or more reference spectra, this typically can be an exceedingly large number, particularly where a large reference library may have tens of thousands of entries. The computational time needed to perform these comparisons can be further magnified if quantitative analysis is to be performed as well as qualitative analysis, i.e., where the relative proportions of component spectra within the unknown spectrum are to be determined as well as their identities. Such quantitative analysis may require that regression be performed between a combination of reference spectra versus the time series of spectra to determine the weighting that each reference spectrum should have to result in a combination which is a best match. As a result, exhaustive spectral matching can sometimes take hours—or even days—to perform, even where dedicated computers or other machines with high-speed processors are used.

Background information on a method of spectrally matching an unknown spectrum using multi-component analysis and of which is incorporated by reference in its entirety herein, is described and claimed in U.S. Pat. No. 7,698,098 B2, entitled, "EFFICIENT SPECTRAL MATCHING, PARTICULARLY FOR MULTICOMPONENT SPECTRA" issued Apr. 13, 2010, to Ritter et al., including the following, "[a]n unknown spectrum obtained from infrared or other spectroscopy can be compared to spectra in a reference library to find the best matches. The best math spectra can then each in turn be combined with the reference spectra, with the combinations also being screened for best matches versus the unknown spectrum. These resulting best matches can then also undergo the foregoing combination and comparison steps. The process can repeat in this manner until an appropriate stopping point is reached, for example, when a desired number of best matches are identified, when some predetermined number of iterations has been performed, etc. This methodology is able to return best-match spectra (and combinations of spectra) with far fewer computational steps and greater speed than if all possible combinations of reference spectra are considered."

Background information on a method of component spectral analysis, is described and claimed in U.S. Pat. No. 7,072,771 B1, entitled, "METHOD FOR IDENTIFYING COMPONENTS OF A MIXTURE VIA SPECTRAL ANALYSIS" issued Jul. 4, 2006, to Schweitzer et al., including the following, "[t]he present invention is directed generally toward the field of spectral analysis and, more particularly, toward an improved method of identifying unknown components of a mixture from a set of spectra collected from the mixture using a spectral library including potential candidates. For example, the present method is directed to identifying components of a mixture by the steps which comprise obtaining a set of spectral data for the mixture that defines a mixture data space; ranking a plurality of library spectra of known elements according to their angle of projection into the mixture data space; calculating a corrected correlation coefficient for each combination of the top y ranked library spectra; and selecting the combination having the highest corrected correlation coefficient, wherein the known elements of the selected combination are identified as the components of the mixture."

SUMMARY OF THE INVENTION

The present invention is directed to an automated method of analyzing a series data file resulting from an evolving sample(s). In particular, using MCR or Multi-component Regression, a series of linearly independent spectra can first be extracted through analysis. Technically, an MCR result is called a "factor" and a set of factors is often produced by MCR; and when recombined, these factors can reproduce the original data set. MCR, as disclosed herein, can then be directed to pass the factors to a Multi-component Search (MCS) routine, which can deconvolute the factors, searched against provided data bases. The end result of such a process enables the identification of each component present in the original data set.

The routine can complete the analysis by performing a spectral correlation of the components identified with the original data set. Essentially, this is done by comparing the component spectra to those in the original data set and providing a value showing how much of that component is present at that time point. The summary of this across the entire time-evolved data set produces a profile representing the time history of the presence of each component. Ultimately, this results in a sequence of profiles showing the time dependence of each component.

The final report can often be customized to consist, if desired, of the spectra extracted, the search results, and the profiles for each identified component. This overcome several issues with the existing technology:

All spectra in the database is processed for information extraction.

The user does not have to possess some initial knowledge of the sample.

The user does not need to have any skills with the analysis software.

The speed of the final analysis is greatly accelerated.

Accordingly, a first aspect of the present application includes a method of analyzing spectra from an evolving sample of which includes: utilizing a spectrometer to obtain a time and/or spatial series set of spectra; estimating by using a computer, one or more qualitative and quantitative constituent components from each of the time and/or spatial series set of spectra by way of a regressive method; and utilizing a computer to pass the estimated one or more qualitative and quantitative constituent components from each of the time and/or spatial series set of spectra into a multi-component search (MCS) algorithm configured to iteratively correlate one or more comparison spectra disposed in one or more spectral libraries to each of the estimated time and/or spatial series set of spectra represented as one or more respective qualitative and quantitative constituent components, wherein the result is an iteratively determined best match time and/or spatial series set of one or more candidate spectra.

A second aspect of the present application includes a system for analyzing spectra from an evolving sample that includes: a spectrometer configured to generate a time and/or spatial series set of spectra; and a computer configured to estimate one or more qualitative and quantitative constituent components from each of the time and/or spatial series set of spectra by way of a regressive method, wherein the computer passes the estimated one or more qualitative and quantitative constituent components from each of the time and/or spatial series set of spectra into a multi-component search (MCS) algorithm configured to iteratively correlate one or more comparison spectra disposed in one or more spectral libraries to each of the estimated time and/or spatial series set of spectra represented as one or more respective qualitative and quantitative constituent components, wherein the result is an iteratively determined best match time series set of one or more candidate spectra.

BRIEF DESCRIPTION OF THE DRAWINGS

FIG. 5 depicts an exemplary output report of candidate spectra that might be presented to a user after the MCR and/or MCR-MCS matching methodology is performed on the estimated pure component time series spectra.

DETAILED DESCRIPTION

Figure 1A:
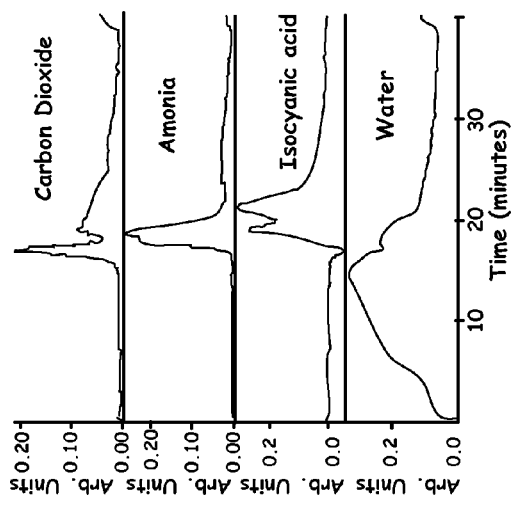
FIG. 1A shows a spectrum of a given time point of a series time file of an exemplary sample.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The most tedious step of analyzing a series data file (e.g., a time series of spectra) is the one-by-one extraction followed by an analysis of the individual spectra, which may themselves be mixtures. Such an analysis methodology is time consuming and requires some skill and "artistry" to carry out effectively. Moreover, such a one-by-one extraction method limits the user to analyzing small regions of a file identified as "interesting" to the user. To overcome such tedium in a novel manner, the embodiments disclosed herein includes an automated process using Multi-Component Regression (MCR), which estimates the pure components in the interrogated sample, to be often followed by a Multi-Component search (MCS) method that utilizes an unbounded (if configured to do so) search criteria of one or more spectral libraries. Such an MCS method is described in the incorporated by reference U.S. Pat. No. 7,698,098 B2, entitled, "EFFICIENT SPECTRAL MATCHING, PARTICULARLY FOR MULTICOMPONENT SPECTRA" issued Apr. 13, 2010, to Ritter et al.

Thus, an MCR-MCS combination method of the present invention provides a beneficial and novel tool to a user that not only simplifies but automates a useful process that provides consistency from user to user. In particular, the MCR-MCS methodologies disclosed herein can provide full and complete analysis of the data set such that even small items that may have been overlooked by conventional methods are now capable of being seen so as to be interpreted in a useful way by the user. For example, a beneficial use of the present embodiments is the overlay of profiles showing the time behavior of the various components. Such a result provides what a customer is seeking, i.e., a deep examination of how the data evolves during the timed event.

For the end user, this means a rapid, complete story can be told. For example, the profiles (what and when) for two or more materials, differing only in some additive can be compared, telling the user what is different. In cases where the same materials are present but the overall process had differed, the time evolution plots can illustrate how the different production process affected the materials. Importantly, the methods of the present invention are available to any skill level of user, meaning pharmaceutical labs with no expertise in, for example, FT-IR analysis of materials, or the basic analytical lab with low-skill users can now obtain high quality results.

Specific Description

The Multivariate-component Resolution (MCR) aspect disclosed herein is directed to a mathematical method of regressively extracting a set of concentration time profiles and estimated spectra of pure components from a time series set of unknown mixture spectra without any beforehand knowledge of the mixture contained in the evolving sample being interrogated. Accordingly, it is to be appreciated that the automated processing nature of the present application begins with MCR so as to extract a series of linearly independent factors from the sequence of collected spectral data. Essentially, the factors represent a distillation of the series of spectra to their constituent parts, i.e., spectra which when combined describe the data. As a non-limiting illustration, such a time-series data set of the MCR method disclosed herein can be used to extract estimated "pure components" (e.g., fluorophores) of a fluorescing sample along with the respective relative concentrations so as to provide the quantitative contributions from such individual estimated "pure" components.

As a method of operation, absorbance spectra measured versus time is thus first obtained by utilizing any number of means as known to those of ordinary skill in the art, such as, but not limited to, thermal gravimetric analysis (TGA) to produce a time series set of spectral data (spectra collected from an evolving sample) similar to that shown in FIG. 1A. The initial objective is to estimate the "pure components" that make up the time series set of spectra.

Accordingly, although Multi-component Regression (MCR) can extract the desired series of linearly independent spectra through the analysis process, it is to be appreciated, however, that the MCR software cannot distinguish between spectra with one component or ten, but can only extract spectra which show independent time evolution. For example, if ammonia and water are evolving from a sample at the same time, the MCR software, as utilized herein, can pull out the spectrum of ammonia plus water, not the separate ammonia and water spectra. On the other hand, if isocyanate is also evolving but at a different moment in time, even if the resultant spectra overlap with the ammonia plus water spectra, the result can show ammonia plus water and isocyanate.

Figure 1B:
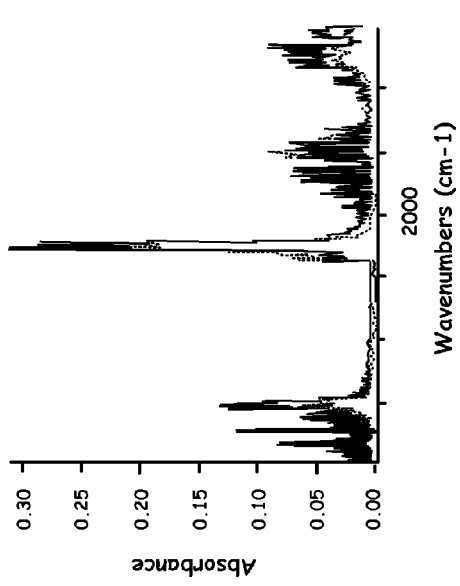
FIG. 1B shows MCR estimated pure component absorbance spectra for carbon dioxide, ammonia, Isocyanic acid, and water resulting from the deconvolution of the spectrum of FIG. 1A.
Figure 1C:
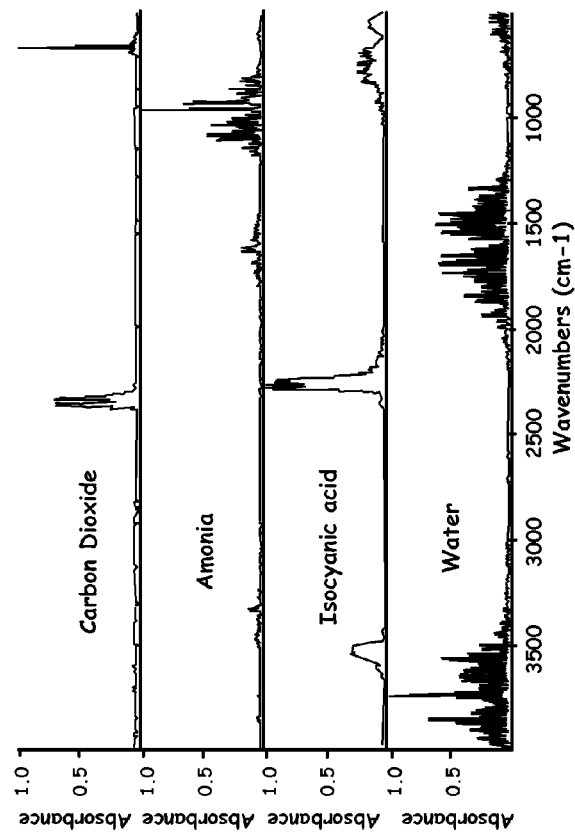
FIG. 1C shows quantification time profiles for the example estimated pure components illustrated in FIG. 1B.

Turning specifically to FIG. 1A, FIG. 1B, and FIG. 1C, the figures illustrated represent exemplary data of Carbon dioxide, Ammonia, Isocynaic acid, and Water inclusive in an evolving epoxy sample as received by instrumentation and thereafter extracted using the Multivariate Curve resolution (MCR) method step of the invention. In particular, the spectra shown in FIG. 1A shows a snapshot in time of absorbance spectra obtained by way of thermal gravimetric analysis (TGA) of the sample. Users can collect such data using a designed front end, producing a series time file of spectra similar to FIG. 1A.

FIG. 1B shows respectively the absorbance spectra of estimated pure components (e.g., Carbon dioxide, Ammonia, Isocynaic acid, and Water) as a result of MCR analysis of the received series time file of spectra, one of which is illustratively shown in FIG. 1A. Finally, FIG. 1C shows resulting MCR produced time profiles for the estimated components shown in FIG. 1B.

As a still general yet more detailed description of the MCR algorithm disclosed herein, a set of absorbance spectra, similar to FIG. 1A, but as measured versus time, is first collected by means known to those of ordinary skill in the art. The MCR embedded software calls the set of absorbance spectra S (spectra x # of data-points). It is to be noted that the initial objective of the MCR software package is to estimate the "pure components" that make up the set of spectra. To start, the pure components are called P (pures x # of data-points) and C (spectra x pores) is deemed the amount of each pure in each spectrum.

As a result, for a given actual spectra of pure components matrix S, where each row correlates to a spectrum of a mixture, the following form is produced:

$$S=PC \quad\quad 1)$$

Here, P and C are the vector matrices with P, as stated above, being the "pure components" (i.e., pures x # of datapoints) and the amount of each pure in each spectrum being C (spectra x pures). In addition, it is to be noted that the "pure components" (i.e., pures x # of datapoints) is desirably about the same as the total number of estimated components resulting from the series time file. Thus, the correlated spectrum resulting from Equation 1 above desirably produces best estimates in terms of how the most dominant individual component intensities are changing in the evolving sample(s).

Moreover, it is also to be noted that the MCR method steps disclosed herein also beneficially utilizes restrictions, such as, for example, unimodality restrictions, but more often non-negativity constraints. As a preferred restriction, a non-negativity constraint is often chosen on the basis of specific knowledge of the data; e.g., that absorbance measurements should be positive, so as to provide for enhanced intensities and sample concentrations in the data that can often be encumbered by measurement ambiguities. Therefore, using non-negativity constraints further restricts C and P to both be non-negative, i.e., $c(i,j)>=0$ and $p(j,k)>=0$; (with i corresponding to number of samples measured spectrophotometrically k times at j wavelengths).

To start the iterative process, MCR has to initially guess the number of components. There have been strategies proposed for estimating the number of components, but in the end there is some arbitrariness in each of the strategies. The technique must estimate both the pure component spectra and the concentrations from a time series set of measured spectra or from a spatial collection of spectra. This is done in an iterative procedure called alternating least squares. The first step is to make an arbitrary guess about the shape of either the pure component spectra or the concentration profiles.

If you arbitrarily guess the pure component spectra, then you solve the least squares problem S=PC for C with the constraint that all $c_{jk}$>=0. This is done by an iterative procedure called Non-Negative Least Squares (NNLS). It results in an estimate of C. This estimate of C, the concentrations for the spectra, is then used to make a new estimate of the pure component spectra, P. That is the problem S=PC is solved by NNLS for P. The fact that the technique is NNLS insures that all $p_{ij}$>=0. The steps re-solving for C and then re-solving for P are continued until the solution converges. This will happen after several iterations. The result will be a least squares like solution for the pure component spectra, P, and the concentrations for the spectra, C that will produce the collection of measured spectra S.

It should be noted that the pure component estimate is an approximation and has not been proven to match the spectrum of any real physical material. However it is a meaningful starting point for an MCS (Multi-Component Search) analysis.

Thereafter, MCR can provide to the user the estimated components and concentrations in charts or plots to show time dependence, as similarly shown in FIGS. 1B (i.e., resulting estimated pure components) and 1C (i.e., resulting concentration time profiles for each estimated pure component).

It is to be appreciated however, as stated above, that the beneficial aspect of the present invention is the capability of integrating the MCR analysis methodology with the MCS (Multi-component Search) algorithm, of which is similarly described in the incorporated by reference U.S. Pat. No. 7,698,098 B2, entitled, "EFFICIENT SPECTRAL MATCHING, PARTICULARLY FOR MULTICOMPONENT SPECTRA" issued Apr. 13, 2010, to Ritter et al. Such an MCS process in general, deconvolutes the individual spectra, as searched against provided for data bases, as to be further detailed below. MCS, thus provides identification of each of the estimated components resultant from MCR by performing a spectral correlation that correlates the individual spectra with original data set. The overall beneficial result is the production of often enhanced accurate estimated components and time profiles similar to that of FIG. 1A and FIG. 1C, i.e., to provide the user with even more confident time dependent information of each component in an evolving sample.

Figure 2:
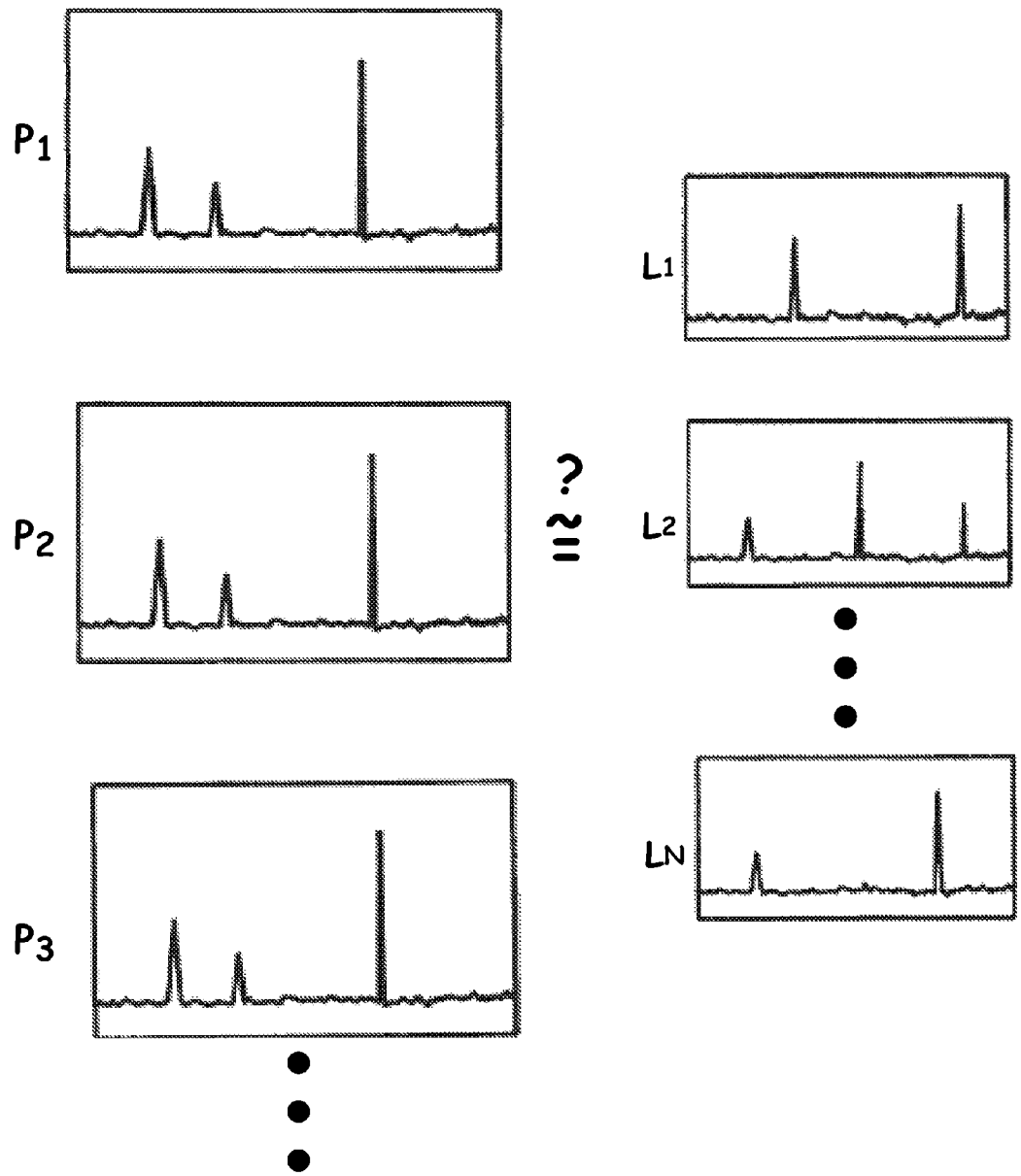
FIG. 2 generally illustrates an exemplary series time file of estimated pure components $P_1$, $P_2$, and $P_3$ resultant from Multi-Component Regression to be thereafter compared to reference spectra $L_1$, $L_2$, and $L_3$ obtained from one or more spectral libraries.

FIG. 2 is schematically now shown to provide a general understanding of the integrated novel aspect of MCR-MCS. Specifically, $P_1$, $P_2$, $P_3$ . . . , as shown in FIG. 2 denotes estimated pure component time series spectra obtained from a spectrometer using MCR software. Such estimated spectral information, i.e., $P_1$, $P_2$, $P_3$ . . . , as provided by MCR are then passed off to the MCS software aspect to be compared to previously obtained reference comparison spectra (denoted as $L_1$, $L_2$, $L_3$ . . . ).

Figure 3:
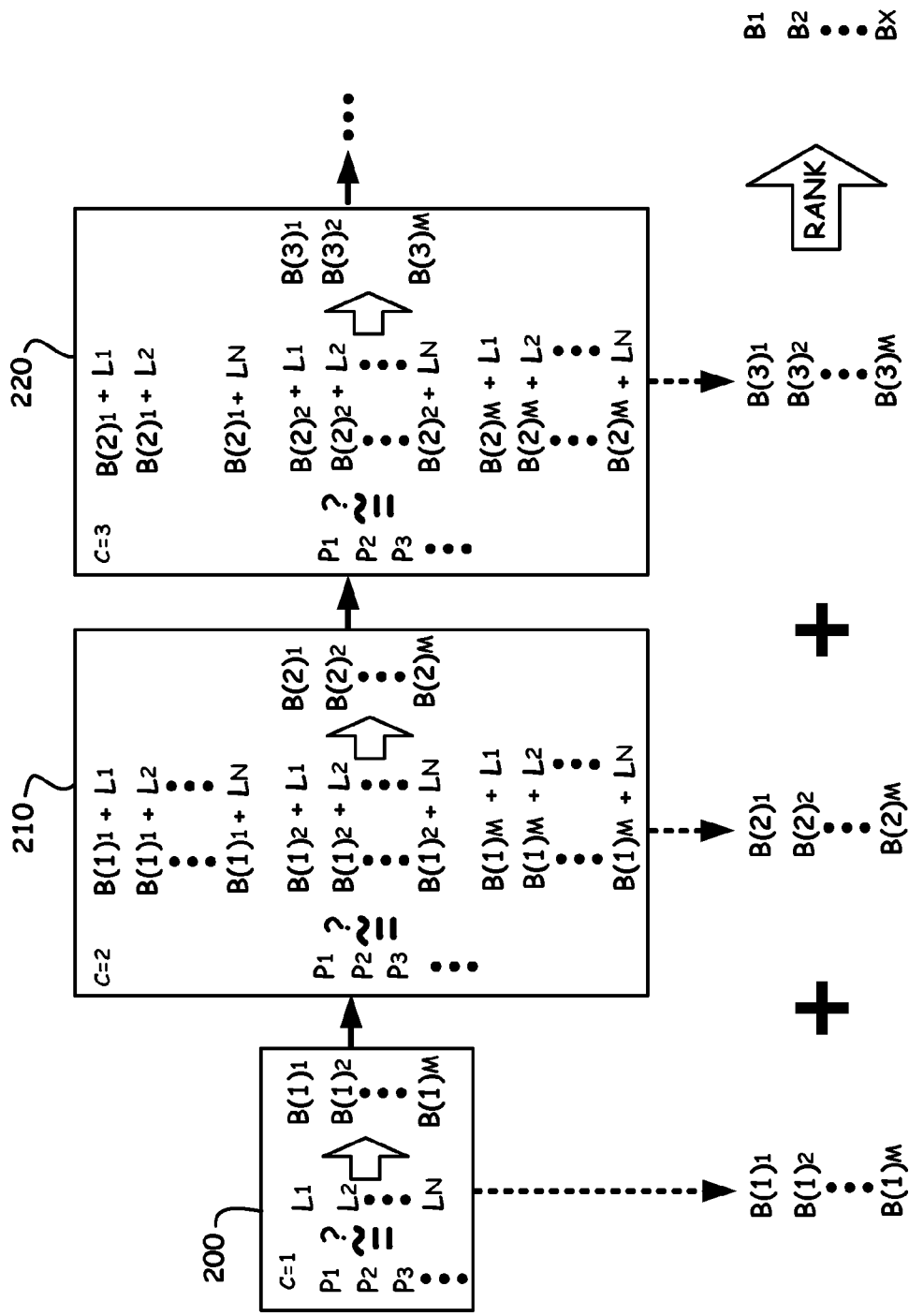
FIG. 3 shows a more detailed version of the illustration shown in FIG. 2. Thus, the estimated pure component spectra (denoted as $P_1$, $P_2$, and $P_3$ . . . ) is shown being compared to reference spectra (denoted as $L_1$, $L_2$, and $L_3$ . . . ) to determine the degree to which the pure spectra correspond to the library spectra. If the pure component spectra match the library spectrum to a desired degree, the comparison library spectrum is considered to be a candidate spectrum ($B_i$).

FIG. 3 somewhat details how the estimated time series pure component spectra $P_1$, $P_2$, $P_3$ . . . of FIG. 2 is compared to some of the comparison (library) spectra to determine the degree to which the pure spectra corresponds to the comparison library spectra $L_1$, $L_2$, $L_3$ . . . , (now shown illustrated in step 200 of FIG. 3).

In particular, once an estimated time series of pure component spectra $P_1$, $P_2$, $P_3$ . . . , as shown illustrated at step 200, is obtained from an optical instrument (e.g., a spectrometer) a database, or any source known to those skilled in the art, and thereafter processed using MCR, as discussed above, comparison library spectra, e.g., $L_1$, $L_2$, $L_3$, can be identified in the following manner.

Initially, comparison spectra, i.e., one or more reference spectra for comparison, are accessed from one or more spectral libraries or other sources. The one or more estimated pure component time series spectra $P_1$, $P_2$, $P_3$ . . . extracted by MCR are then compared to at least some of the comparison spectra to determine the degree to which the time series of spectra correspond to the one or more comparison spectra. If the estimated pure component time series spectra $P_1$, $P_2$, $P_3$ . . . , corresponds to one or more comparison spectra to a desired degree, as by meeting or exceeding some user-defined or preset correspondence threshold, the one or more comparison spectrum is regarded as being identified as one or more candidate spectra $B(1)_1$, $B(1)_2$, . . . $B(1)_M$, as long as the correspondence threshold is not set too high. If no candidate spectra are identified, the correspondence threshold can be set to a lower value.

Next, the possibility that any of the estimated pure component time series spectra might have arisen from a multi-component mixture is considered. New comparison spectra are generated, with each comparison spectrum being a combination of one of the previously identified candidate spectra and one of the comparison spectra from the spectral libraries or other sources. The estimated one or more pure component time series spectra is then again compared to at least some of these new comparison spectra to determine the degree to which the estimated pure component time series spectra corresponds to the new comparison spectra. This step is schematically illustrated at 210 in FIG. 3, wherein any number of the estimated pure component time series spectra $P_1$, $P_2$, $P_3$ . . . , is compared to new comparison spectra:

$B(1)_1+L_1, B(1)_1+L_2, \ldots B(1)_1+L_N$ (i.e., the first of the previously identified candidate spectra from step 200 in FIG. 3 combined with each of the comparison spectra from the spectral libraries or other sources);

$B(1)_2+L_1, B(1)_2+L_2, \ldots B(1)_2+L_N$ (i.e., the second of the previously identified candidate spectra from step 200 combined with each of the comparison spectra from the spectral libraries or other sources); and so forth, until the estimated pure component time series spectra is compared to new comparison spectra:

$B(1)_M+L_1, B(1)_M+L_2, \ldots B(1)_M+L_N$ (i.e., the last of the previously identified candidate spectra from step 200 combined with each of the comparison spectra from the spectral libraries or other sources).

Where these comparisons find that, for example, any one of the new comparison spectra has a desired degree of correspondence to the estimated pure component time series spectra $P_1$, $P_2$, $P_3$ . . . , (as by meeting or exceeding the correspondence threshold), the new comparison spectrum is regarded to be a new candidate spectrum. These new candidate spectra are depicted in FIG. 3 at step 210 as $B(2)_1$, $B(2)_2$, . . . $B(2)_M$. (It is understood that if desired, M in step 210 need not be equal to M in step 200, i.e., the number of candidate spectra in step 210 need not be the same as the number of candidate spectra in step 200.) Here each candidate spectrum $B(2)_1$, $B(2)_2$, . . . $B(2)_M$ represents two components, i.e., two combined reference spectra obtained from a spectral library or other source.

The foregoing step can then be repeated one or more times in an unbounded fashion if desired, with each repetition using the candidate spectra identified in the foregoing step to generate new comparison spectra. This is exemplified by step 220 in FIG. 3, wherein the candidate spectra $B(2)_1, B(2)_2, \ldots B(2)_M$ from step 210 are used in combination with the comparison spectra $L_1, L_2, \ldots L_N$ from the spectral libraries or other sources to generate new comparison spectra. Comparison of the estimated pure component time series spectra $P_1, P_2, P_3 \ldots$, with these new comparison spectra in turn identifies new candidate spectra $B(3)_1, B(3)_2, \ldots B(3)_M$ (wherein M again need not be equal to M in steps 210 and/or 200). Repetition may cease when the candidate spectra include some desired number of components, e.g., once the new comparison spectra include a desired number of combined comparison/reference spectra obtained from a spectral library or other source.

Figure 4:
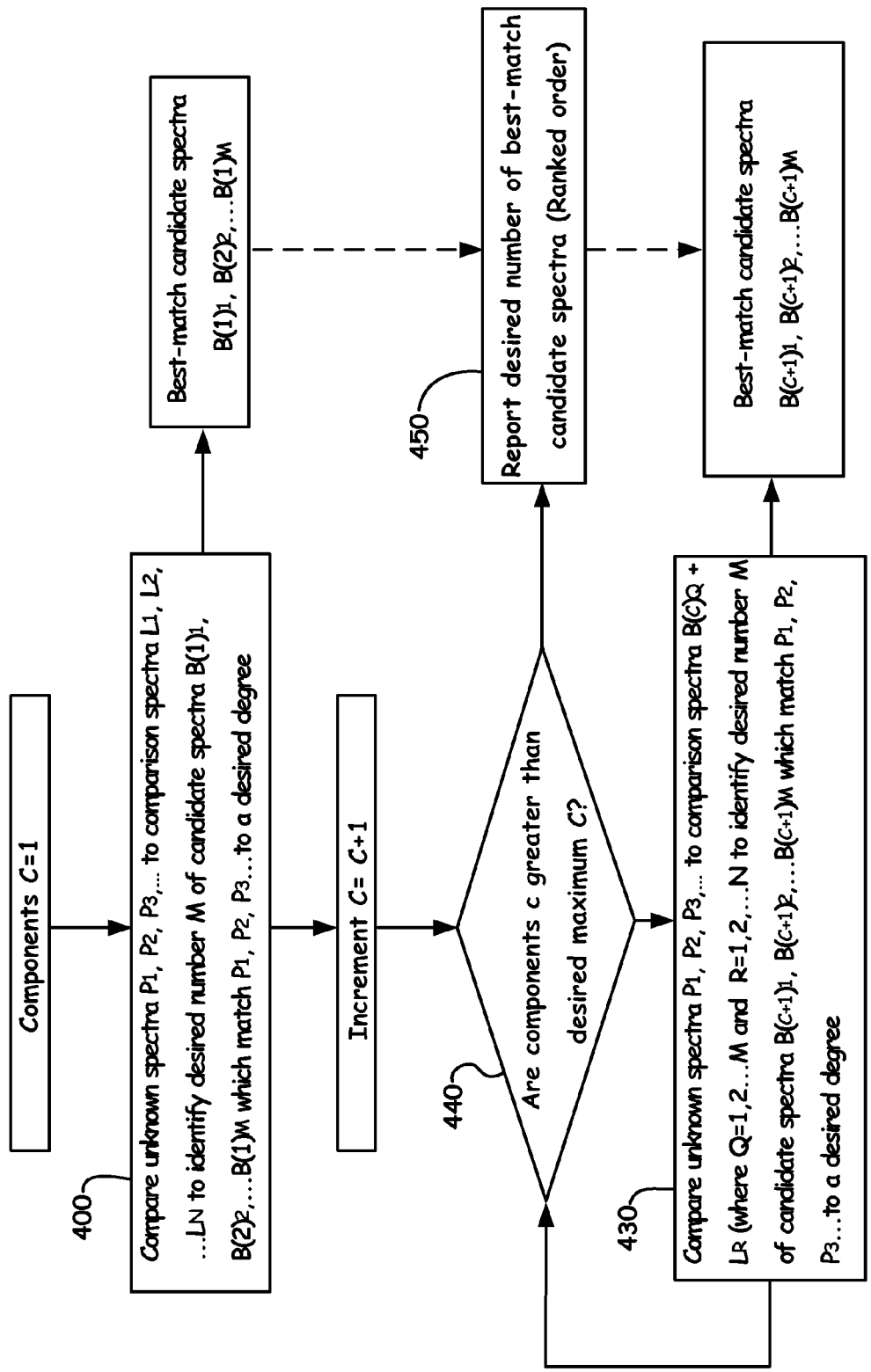
FIG. 4 shows a flowchart depicting the matching methodology of FIG. 3, wherein box 400 is equivalent to step 200 of FIG. 3, box 430 is equivalent to steps 210 and 220 of FIG. 2 (as well as future repetitions of these steps), and the condition box 440 applies a stopping condition for reporting candidate spectra to a user (at box 450).

This condition is illustrated in the flowchart of FIG. 4, wherein step 400 is equivalent to step 200 of FIG. 3, step 430 is equivalent to steps 210 and 220 of FIG. 3 (as well as future repetitions of these steps), and the condition box 440 evaluates the number of components c in the candidate spectra and ceases repetition once some maximum number C is reached. Alternatively or additionally, repetition may cease when some desired number of candidate spectra are identified; when one or more candidate spectra are identified which match the unknown spectrum by at least some qualifying correspondence value (the qualifying correspondence value being greater than the threshold correspondence value), as discussed below; or when other suitable conditions arise.

At least some of the candidate spectra may then be presented to a user, with the candidate spectra preferably being presented to the user in ranked order such that those candidate spectra having greater correspondence to the unknown spectrum are presented first (as depicted at step 450 in FIG. 4). An exemplary format for an output list of candidate spectra that might be presented to a user is illustrated in FIG. 5. Here, details regarding the unknown spectrum are given in the heading of the output list, followed by details of the candidate spectra. The first listed candidate spectrum—listed with a rank/index of 1—is a spectrum for polystyrene film, and has a match metric (roughly equal to a "percentage of match") of 99.58 versus the unknown spectrum. The spectral library or other source of this candidate spectrum is also listed (here "User Example Library"), as is its location within the library/source (at "Source Index" no. 2, i.e., it is the second spectrum provided in the "User Example Library"). The second listed candidate spectrum is actually a combination of three spectra from spectral libraries or other sources—a Toluene (Transmission Cell) spectrum, an ABS Plastic (ATR Corrected) spectrum, and Polytetrafluouroethylene Film spectrum—wherein these spectra, when combined in appropriate proportions (as discussed below), yield a 68.97 match metric with the unknown spectrum. Their cumulative match metrics are also presented, with Toluene having is 56.96 match metric, Toluene and ABS together having a 68.92 match metric, and Toluene, ABS, and Polytetrafluouroethylene collectively yielding the 68.97 match metric. Again, the libraries or other sources of these spectra are provided along with an indication of the location of each spectrum within its library/source.

Additional metrics are also preferably provided with the output list, in particular, the weight of each comparison spectrum (each component/reference spectrum) within the candidate spectrum, i.e., the scaling factor used to adjust each comparison spectrum to obtain the best match with the unknown spectrum. For example, the first listed candidate spectrum (Polystyrene Film) has a weight of 5.4195, meaning that the unknown spectrum is estimated to have 5.4195 times the polystyrene content of the sample from which the candidate spectrum was obtained. The second listed candidate spectrum contains different weights of toluene, ABS, and polytetrafluouroethylene, with these weights being determined by regression analysis of the comparison spectra versus the unknown spectrum during the aforementioned comparison step (i.e., the various component/reference spectra within a comparison spectrum are proportioned to attain the best match to the unknown spectrum during comparison). Thus, the user may be provided with an at least approximate quantization of the components within the unknown spectrum.

The methodology above can be said to find "best-match" reference spectra, combine the best-match spectra to other reference spectra, and then identify further best-match spectra from these combinations (with the methodology iteratively continuing from the foregoing combination step). It is therefore seen that rather than comparing all possible combinations of reference spectra $L_1, L_2, \ldots L_N$, the methodology can consider far fewer combinations, basically by pruning out the reference spectra which have less similarity to the unknown spectrum. As a result, the methodology returns high-quality matches in far shorter time than in methods that consider all combinations, particularly where large numbers of reference spectra are used and where the unknown spectrum is reviewed for larger combinations of component/reference spectra—in some cases, returning results in minutes where hours were previously needed.

Prior to performing the aforementioned comparisons between the estimated pure component time series spectra and comparison spectra, the invention may perform one or more transforms on one or both of the estimated pure component time series spectra and comparison spectra to expedite and/or increase the accuracy of the comparison process, or otherwise enhance data processing. As examples, the invention might perform one or more of data smoothing (noise reduction), peak discrimination, rescaling, domain transformation (e.g., transformation into vector format), differentiation, or other transforms on spectra. The comparison itself may also assume a variety of forms, as by simply comparing intensities/amplitudes across similar wavelength ranges between unknown and comparison spectra, by converting the unknown and comparison spectra into vectorial forms and comparing the vectors, or by other forms of comparison.

Additionally, the methodology described above can be modified to further expedite the identification of candidate spectra. As one example of such a modification, when generating a new comparison spectrum by combining a previously-identified candidate spectrum and a comparison spectrum obtained from a spectral library or other source, the combination might be skipped or discarded (i.e., deleted or not counted as a potential new candidate spectrum) if the candidate spectrum already contains the comparison spectrum.

To more specifically illustrate, consider the situation where comparison spectrum $L_1$, which is obtained from a spectral library, is selected as $B(1)_1$ in step 200 (FIG. 3) owing to a sufficient match with unknown spectra. In the next iteration at step 210, the new comparison spectrum $B(1)_1 + L_1$ can be skipped or discarded since it is equivalent to $L_1 + L_1$ (i.e., reference spectrum $L_1$ combined with itself, which will merely again result in $L_1$). Thus, by avoiding the generation and/or use of comparison spectra which have redundant component spectra, the methodology can reserve computation time for comparison spectra which are more likely to yield new candidate spectra.

As another example of a modification that can be implemented to expedite the identification of candidate spectra, if a candidate spectrum matches the unknown spectrum by at degree greater than or equal to some "qualifying" correspondence value—this qualifying correspondence value being greater than the threshold correspondence value—the comparison spectra therein (i.e., its component spectra) can be excluded from any later generation of new comparison spectra. In essence, this measure takes the approach that if a candidate spectrum is already a very good match for an unknown spectrum (e.g., if it has a qualifying correspondence value of above 95%), this may be sufficient, and there is no significant need to determine whether the match might be made even higher if the candidate spectrum was combined with other spectra.

Another modification that can be made to expedite the identification of candidate spectra applies in the special case where one or more of the components of the unknown spectrum are known—for example, when monitoring the output of a process which is intended to generate a material having known components in a predetermined quantity. In this case, during the first round of comparison (step 200 in FIG. 3, step 400 in FIG. 4), the candidate spectra $B(1)_1, B(1)_2, \ldots B(1)_M$ can simply be set to the spectra for the known components. Executing the remainder of the method will then serve to identify any additional components (i.e., impurities) that may be present, as well as the relative proportions of the various components.

As stated above, if the correspondence threshold is set too high, i.e., the degree of match required between the estimated one or more pure component time series spectra and a comparison spectrum for the comparison spectrum to be deemed a candidate spectrum, the result can be to yield no candidate spectra. Typically, a value of 90% correspondence is suitable for the correspondence threshold, though this value might be better set lower or higher depending on the details of the spectra under consideration.

It is also possible to set the correspondence threshold to zero (or to a value near zero), in which case a candidate spectrum can thus result from each comparison spectrum. For example, if the correspondence threshold is set to zero in step 200 of FIGS. 3-4, M=N and $B(1)_1, B(1)_2, \ldots B(1)_M$ is to then each correspond to one of $L_1, L_2, \ldots L_N$. In this case, some of the candidate spectra can in reality be poor candidates because of poor matching with the unknown spectrum. It is then useful to rank the candidate spectra in order of highest correspondence to lowest correspondence, and then first consider those candidate spectra with highest correspondence when performing any subsequent steps. In this case, to reduce computations, it can be useful to discard the candidate spectra with lowest correspondence when performing any subsequent steps. For example, one might keep only the top 10%, 25% or 50% of the candidate spectra having highest correspondence, and to use these in subsequent steps.

It is expected that the invention can be implemented in spectral identification software for use in computers or other systems (e.g., spectrometers) which receive and analyze spectral data. Such systems may include portable/handheld computers, field measurement devices, application specific integrated circuits (ASICs) and/or programmable logic devices (PLD) provided in environmental, industrial, or other monitoring equipment, and any other systems wherein the invention might prove useful.

As an additional embodiment, the following non-limiting example illustrates a beneficial user output interface aspect that can be utilized with the methods disclosed herein. It is to be appreciated that a highly related problem that can be potentially solved with the present embodiments involves the analysis of two similar materials. Two example scenarios: First, a gasket or o-ring from one batch fails while that from another batch works fine. Second, competitor B has introduced a product chemically similar to one made by competitor A, and A wishes to understand the differences in the processing. In both cases, TGA-IR is an often insightful beneficial method to be implemented, with qualitative and quantitative data being provided.

A "light box" (i.e., digitally overlaid (or presented side by side)), extension of the invention can thus be beneficially additionally provided which involves performing a coupled analysis not sequential but simultaneous) on the two data sets. The end result can be a sequence of compositional information and profile information. The output interface can provide views of the search results and views of the time evolution profiles of those components. An important aspect is differences between these comparisons.

If the analyses are configured to be done sequentially, the ordering of the search results and the number of components found can potentially differ, making comparison more complex. By performing the analysis in a coupled manner, the results are linked both by composition and rank ordering of the search results. This permits the "light box" approach where the results are digitally overlaid (or presented side by side) for easy comparison.

Referring back to the two scenarios, in the first case the overlay view may show that one component is missing—a formulation error—or that the temperature evolution profile for one or more component is shifted between the two—a processing error. In the second case, the deformulation profiles allows the known product with known characteristics from company A to be compared with the unknown company B material; either composition or processing differences are once again brought out. Ultimately, this represents the "final answer" for which the entire analysis has been reaching—what is different about these two samples.

Additionally, while the invention has generally been described as being usable in the context of spectral matching for molecular spectrometers, it may alternatively or additionally be used in mass spectroscopy, X-ray spectroscopy, or other forms of spectroscopy. It might additionally be useful in other forms of measurement analysis wherein signals are measured versus reference values, in which case such signals and reference values may be regarded as "spectra" in the context of the invention.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A method of analyzing spectra from an evolving or changing sample, the method comprising:
    utilizing a spectrometer to obtain a time series set of spectra;
    estimating by using a computer, at least one qualitative and quantitative constituent component from each of said time series set of spectra by way of a regressive method; and
    utilizing a computer to pass said estimated at least one qualitative and quantitative constituent component from each of said time series set of spectra into a multi-component search (MCS) algorithm configured to iteratively correlate at least one comparison spectrum disposed in at least one spectral library to each of said estimated time series set of spectra represented as at least one respective qualitative and quantitative constituent component, wherein the result is an iteratively determined time series set of at least one candidate spectrum for spectral identification of the sample, and said MCS search algorithm, which iteratively correlates at least one candidate spectrum, is further configured for:

generating at least one new comparison spectrum, wherein each of said new comparison spectrum is a combination of one of a previously identified candidate spectra and one of a comparison spectra from a spectral library source, and comparing said estimated at least one qualitative and quantitative constituent component from each of said time series set of spectra to selected said new comparison spectrum to determine a degree of correspondence; and repeating said generating and comparing steps above until a number of said set of at least one candidate spectrum is identified which matches said estimated at least one qualitative and quantitative constituent component from each of said time series set of spectra by at least some qualifying correspondence value until a maximum number of constituent components is reached in selected said time series set of at least one candidate spectrum.

2. The method of claim 1, further comprising: presenting said iteratively determined time series set of at least one candidate spectrum as time evolution profiles of said at least one qualitative and quantitative constituent component.

3. The method of claim 1, wherein said regressive method within said estimating step comprises a multi-component regression (MCR) algorithm.

4. The method of claim 1, wherein at least one transform is performed on at least one of said estimated at least one qualitative and quantitative constituent component from each of said time series set of spectra and said at least one comparison spectrum.

5. The method of claim 1, further comprising skipping or discarding said comparing step if said previously identified candidate spectrum already contains one of a comparison spectrum from a spectral library source.

6. The method of claim 3, wherein said multi-component regression (MCR) algorithm comprises a unimodality constraint of said obtained time series set of spectra.

7. The method of claim 3, wherein said multi-component regression (MCR) algorithm comprises a non-negativity constraint of said obtained time series set of spectra.

8. The method of claim 7, wherein said multi-component regression (MCR) algorithm comprises a Non-Negative Least Squares (NNLS) iterative procedure to provide for said at least one qualitative and quantitative constituent component from each of said time series set of spectra.

9. A system for analyzing spectra from an evolving or changing sample, comprising:

a spectrometer configured to generate a time series set of spectra; and a computer configured to estimate at least one qualitative and quantitative constituent component from each of said time series set of spectra by way of a regressive method, wherein said computer passes said estimated at least one qualitative and quantitative constituent component from each of said time series set of spectra into a multi-component search (MCS) algorithm configured to iteratively correlate at least one comparison spectrum disposed in at least one spectral library to each of said estimated time series set of spectra represented as at least one respective qualitative and quantitative constituent component, wherein the result is an iteratively determined time series set of at least one candidate spectrum for spectral identification of the sample, and said computer is further configured to:

a. generate at least one new comparison spectrum, wherein each of said new comparison spectrum is a combination of one of a previously identified candidate spectra and one of a comparison spectra from a spectral library source;

b. compare said estimated at least one qualitative and quantitative constituent component from each of said time series set of spectra to selected said new comparison spectrum to determine a degree of correspondence; and c. repeat the generating and comparing steps above until a number of said set of at least one candidate spectrum is identified which matches said estimated at least one qualitative and quantitative constituent component from each of said time series set of spectra by at least some qualifying correspondence value until a maximum number of constituent components is reached in selected said time series set of at least one candidate spectrum.

10. The system of claim 9, wherein said computer is further configured to present said iteratively determined time series set of at least one candidate spectrum as time evolution profiles of said at least one qualitative and quantitative constituent component.

11. The system of claim 9, wherein said computer skips comparing if said previously identified candidate spectrum already contains one of a comparison spectrum from a spectral library source.

* * * * *